US006749597B2

(12) United States Patent
Frank

(10) Patent No.: US 6,749,597 B2
(45) Date of Patent: *Jun. 15, 2004

(54) RESPIRATORY INFECTION TREATMENT DEVICE

(76) Inventor: Steven R. Frank, 11192 Twin Spruce Rd., Golden, CO (US) 80403

(*) Notice: Subject to any disclaimer, the term of this patent is extended or adjusted under 35 U.S.C. 154(b) by 0 days.

This patent is subject to a terminal disclaimer.

(21) Appl. No.: 10/320,956

(22) Filed: Sep. 11, 2002

(65) Prior Publication Data

US 2003/0153880 A1 Aug. 14, 2003

Related U.S. Application Data

(63) Continuation of application No. 09/718,520, filed on Nov. 21, 2000, now Pat. No. 6,454,754, which is a continuation of application No. 09/182,581, filed on Oct. 29, 1998, now abandoned.

(51) Int. Cl.[7] .............................................. A61M 31/00

(52) U.S. Cl. .................... 604/500; 604/48; 128/200.14; 424/45; 424/618; 516/97

(58) Field of Search ............................ 604/500, 19–21, 604/48, 93.01; 128/200.14; 424/45, 618; 516/97

(56) References Cited

U.S. PATENT DOCUMENTS

| | | | | |
|---|---|---|---|---|
| 5,785,972 A | * | 7/1998 | Tyler | 424/764 |
| 6,454,754 B1 | * | 9/2002 | Frank | 604/500 |

* cited by examiner

*Primary Examiner*—Loan H. Thanh
*Assistant Examiner*—Jeremy Thissell
(74) *Attorney, Agent, or Firm*—Welsh & Flaxman LLC

(57) ABSTRACT

A device and method for treating an illness or infection in the repiratory tract of a body is provided. The device administers an antimicrobial mist directly to the tissues to be treated, which coats the tissues in the respiratory tract where the infection is colonizing. The administration of the mist is reapplied in order to maintain a predetermined antimicrobial tissue density concentration of a uncompounded silver colloid suspended antimicrobial substance for a predetermined time period.

7 Claims, 1 Drawing Sheet

RESPIRATORY INFECTION TREATMENT DEVICE

The present application is a continuation of patent application Ser. No. 09/718,520 filed on Nov. 21, 2000 now U.S. Pat. No. 6,454,754 which is a continuation of patent application Ser. No. 09/182,581, filed on Oct. 29, 1998, entitled "Electrolytic Substance Infusion Device", now abandoned.

BACKGROUND OF THE INVENTION

1. Field of the Invention

This invention relates generally to a treatment device for respiratory infections, more particularly, it relates to a treatment device which delivers metal colloids into the upper and lower respiratory tracts in a manner which terminates viral and bacterial respiratory infections by coating the infected tissues with antimicrobial metal colloids at predetermined tissue densities for predetermined time periods.

2. Description of the Prior Art

There are a number of viral and bacterial infections, which gain entry to the body and subsequently thrive in the moist and well vascularized membranes of the nasal passageway, the sinuses and the lungs. Presently, when these infections occur, the infected party is prescribed systemic doses of antibiotics or antiviral agents. These agents are most often ingested in quantities of several grams per day in order to achieve the systemically diluted tissue densities of thirty (30) to fifty (50) micrograms per milliliter.

The unfortunate consequence of this dosing is that in the case of antivirals, a large number of liver cells or kidney cells will be damaged. When the agent is an antibiotic, the natural fauna of bacteria through out the body is dramatically altered allowing opportunistic bacteria to over-load an area and often resulting in secondary infections in other areas or fungal infections. Indeed, when a therapeutic agent that is intended to operate in the nose, sinuses or lungs is required to be administered systemically, the required dose and body-burden is quite large.

Often times, the infection being treated does not respond to the first antibiotic treatment and multiple courses of various antibiotics are sequentially administered further burdening the body and detrimentally distorting the natural bacterial balance. This usually leads to prolonged feelings of malaise for the treated subject and peripheral ailments such as yeast infections, low energy and diarrhea.

The treatment of respiratory infections by means of an appropriate delivery of uncompounded silver colloid to the infected tissue overcomes both of the problems of the currently administered protocol by dramatically reducing the amount of the antimicrobial required and by administering it directly to the infected tissue.

Presently, silver colloids are utilized occasionally to treat infections but the protocols and administration mechanisms are usually a medicine dropper or a teaspoon. The method utilized is to "drink" a small amount (a teaspoon) of silver colloid. This results in a systemic dilution of ionic silver on the order of nanograms per milliliter of tissue throughout the entire body. Additionally, the commercially available preparations tend to be of concentrations too low to be effective. They tend to be on the order of less than 10 ppm. Laboratory studies have shown for years that this level of concentration in infected tissue has no measurable antimicrobial effects. There would be no measurable antimicrobial effects even if the concentration level was increased when orally ingested, because the silver easily becomes compounded and less effective.

Pure silver refers to silver in it's uncompounded metalic state. This silver has excess positive charge as Ag+. Ionic silver is often referred to as a silver atom which is in it's metalic state of Ag+, but since this is reactive, it usually is found in agglomerated balls of atoms with a excess positive charge greater than one. Otherwise, it reacts with nearby anions to produce a compound.

Compound silver occurs when the ionic silver is allowed to react chemically with anions and produce a reduced compound. This is what occurs when ionic silver binds with oxygen to produce silver-oxide (AgO). It also occurs when silver binds with chlorine (a common free anion in the body) and produces silver chloride (AgCl). This "compound" will precipitate as it is insoluable in water.

Since silver in it's ionic state is carrying a positive charge it wants to react with an anion and form a compound. It willing rapidly bind with proteins and polysaccharides (sugars) that are normally found in the body. This binding however, renders it inactive as an antimicrobial. In much the same way, Silver Chloride, Silver Nitrate, Silver Acetate, Silver Sulfadiazine and other compounds are far less antimicrobial than "Pure Ionic Silver", which is well known based upon the research in this area.

A colloid is a suspension of particles of one substance within another substance. An aqueous colloidal suspension of silver is one in which small particulate silver is suspended in water. Since water is stable and contains no excess negative charge, the silver ions do not bond with it. This keeps it from compounding and allows it to remain in a highly reactive and antimicrobial form. When this ionic colloid is applied to body tissues, it immediately begins to compound with proteins, polysaccharides and free anions.

Therefore, the present invention overcome the deficiencies of the prior art and creates a new protocol for making effective use of uncompounded silver colloids.

SUMMARY

The present invention is a means and protocol for treating an illness or infection of respiratory tissue of a body. The device consists of either a nebulizer or spray device for making a mist of appropriately sized droplets of fluid. This fluid consists of the appropriate concentration of pure silver colloid. The means requires administration of this colloid with these mechanical dispensing mechanisms according to the prescribed replenishment protocol. The result is to maintain a ten (10) microgram or greater concentration of ionic silver (a known antimicrobial) in the infected tissue. This is a highly effective means of dispatching disease without subjecting the entire body to a high level of toxic antiviral pharmacological agents or antibiotics.

The administration of pure ionic silver colloid in this manner makes it possible to more effectively treat an infection with 10,000 times less antimicrobial agent than currently prescribed techniques or tools require. The results seen have surpassed the efficacy of both pharmaceutical antivirals and antibiotics on sinus infections and lower respiratory infections. The effectiveness of this therapy on the common cold has produce results far better than any other known treatment typically terminating a cold in twelve (12) to twenty-four (24) hours when used at the first signs of infection.

In this manner, it represents a quantum leap in the treatment of respiratory illnesses. It utilizes a benign substance (silver colloid) to effectively treat major infections and yields no known observable adverse side effects. An additional benefit of this invention is that since the treatment is so benign to the subject, it can be used prophylactically. When a person is being exposed to an environment of contagious airborne microbes, they can use the nasal spray regularly to dispatch the inhaled infectious germs before they can multiply sufficiently to overcome the immune systems and produce a symptomatic illness. This level of preventative therapy has never before been available against airborne infectious disease.

Antimicrobial is used to indicate anti-viral, anti-fungal and anti-bacterial.

DETAILED DESCRIPTION OF THE PREFERRED EMBODIMENTS

Figure 1:
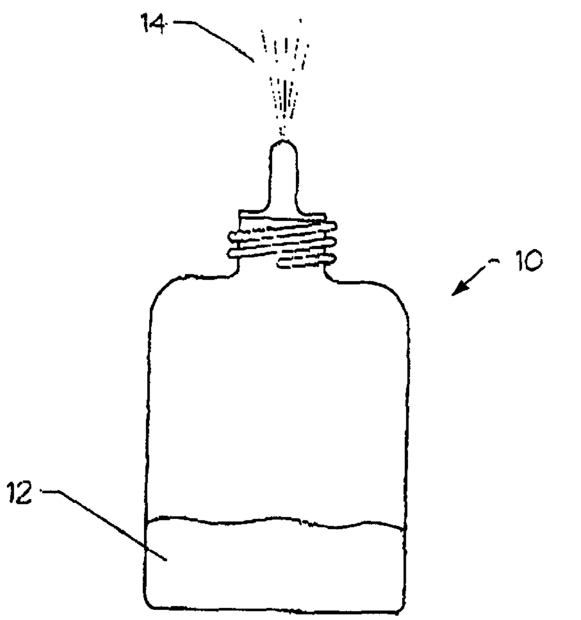
FIG. 1 is a side view illustrating a nasal spray bottle embodiment of present invention, constructed in accordance with the present invention, for treating respiratory ailments and infections of the lower respiratory tract.

In the nasal spray bottle 10 of the present invention, as illustrated in FIG. 1, the agent 12 (typically twenty (20) ppm uncompounded aqueous silver colloid) is dispensed by the user squeezing the bottle when it is placed within the nasal passageway (not shown) of a user (not shown). The action of dispensing the agent 12, accompanied by an inhalation of the user coats the nasal passageways with the agent 12 thereby rendering the nasal passageways antiseptic. For treating infections of the sinus and nasal passage ways, large droplets of the spray bottle aerosol (~100 microns) are appropriate as they are intended to coat the nasal passages.

Figure 2:
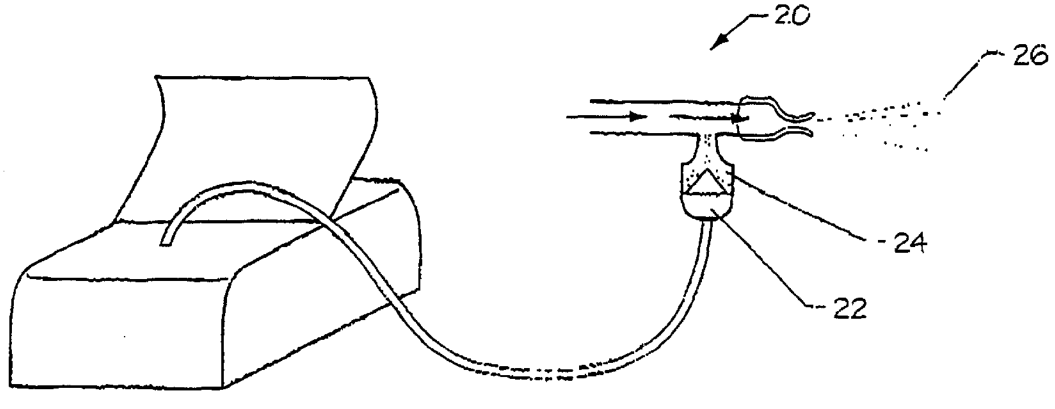
FIG. 2 is a side view illustrating a nebulizer embodiment of the present invention, constructed in accordance with the present invention, for treatment of colds and sinus infections.

In the nebulizer 20 of the present invention, as illustrated in FIG. 2, the agent 22 (typically forty (40) to sixty (60) ppm uncompounded aqueous silver colloid) is placed in the nebulizer chamber 24. The nebulizer 20 then produces droplets of less than ten (10) microns in diameter, which are inhaled by the user receiving therapy. The small droplets of agent 22 are able to negotiate the pharyngeal bends without significant impact loss and coat the bronchi of the lungs where some airborne virus and bacteria colonize, thereby terminating the infection. The smaller droplets are required here to allow access to the furthest reaches of the bronchi. For this treatement, 3 to 5 micron droplets are preferred. It should be noted though, that too small a droplet (1 micron or less) is undesireable as it is too easily exhaled before it has an opportunity to adhere to the lung or bronchi surface. This exhalation of product would reduce the effectiveness of the therapy.

Various Preferred Embodiments of the Present Invention

Nasal Spray Device

As illustrated in FIG. 1, a manner of treating colds and sinus infections when they reside primarily in the upper respiratory regions such as the sinuses and the nasal passages ways. This embodiment utilizes atomizing spray bottles 10, which produce a mist 14. This mist 14 is inhaled through the nose at least every fifteen (15) to sixty (60) minutes. The mist 14 is comprised of a colloidal suspension of uncompounded silver such as a twenty (20) ppm aqueous silver colloid. The mist spray 14 is comprised of droplets large enough so that they predominantly contact the nasal membranes and coat the passages ways therein, generally in the range of 100 microns. The colloidal suspension migrates into the sinus passages where it kills bacteria. In the nasal passageways, it serves to terminate viral infections such as colds. In the case of treating colds, the silver colloid inhibits viral reproduction in the tissue cells of the nasal passages. In the case of sinusitis, the silver migrates into the sinuses and attenuates the bacterial population there allowing the bodies natural immune system to return the region to a state of balance.

For the nasal environment, there is a great deal of mucosal flow carrying away the silver. Therefore, in the preferred of this therapy one needs to apply approx. 200 microliters to the nostrils every 15 minutes to refresh the environment.

The airborne droplets of pure silver colloid are in a high enough concentration so that when inhaled, they coat the tissues where the infection is propagating. In the case of treating colds, the nasal spray bottle delivers a sufficiently small droplet mist and is convenient to use. By administering at least twenty (20) ppm pure silver colloid directly to the nasal passageway, where the virus is multiplying, a sufficiently high tissue concentration (greater than or equal to ten ($\geqq$10) micrograms/ml) is maintained only in the area of the infection dramatically reducing amount of agent required.

Nebulizer Device

As illustrated in FIG. 2, a manner of treating microbial infections which have already reached the lungs or the throat, is provided. In this embodiment, the infusion device or nebulizer device 20 of the present invention includes nebulizer device 20 having a colloidal suspension preparation 22 containing ionic silver within a carrier, e.g., water. The colloidal suspension 22 generally of forty (40) to sixty (60) ppm silver is administered with an ultrasonic nebulizer, aerosol, or spray atomizer 24 to combat infections of the lungs such as bronchitis, chest colds, anthrax, and tuberculosis, for instance. By propelling the colloidal suspension 22 of the silver in this nebulized flow of moist air, any tissue that can be reached and infected by airborne virus can also be reached by the antimicrobial agent. The nebulizer device 20 provides small droplet size mist 26, typically less than ten (10) microns, which can negotiate the esophagus and reach the lower respiratory tract. Inhalation through the nose can allow treatment of the nasal passageways and has been shown to eliminate colonization of cold virus and even overcoming severe sinus infections. The smaller droplets are required to allow access to the furthest reaches of the bronchi. It is noted that too small a droplet is undesirable as it is too easily exhaled before it has had an opportunity to adhere to the lungs or bronchi surface. The exhalation of the silver would reduce the effectiveness of the therapy.

Some silver colloids are held in higher suspensions by means of attaching the silver ions to proteins. These are called “mild silver proteins”. It is unfortunate that the very process of binding the ions to the proteins to increase the available concentration also reduces the effectiveness by rendering the ions less bio-active. In fact, the achieved higher concentrations (typically two-hundred and fifty (250 ppm)) are less effective than the twenty (20) ppm pure silver colloids tested by the inventor. As stated above these higher concentration solutions may have more silver but is compounded and not pure or uncompounded. It is important to use twenty (20) ppm or greater pure silver colloids to achieve enough antimicrobial activity when diluted by body fluids such as mucus and interstitial fluids. For lower respiratory infections where the surface area of the lungs is very large and there is plenty of fluid, concentrations of forty (40) to sixty (60) ppm pure silver colloid are required.

Since mucosal flow will carry the inhaled coating of silver colloid away in less than an hour, a critical part of the process which has not been practiced is the appropriate re-administration protocol. It is necessary to replenish the area of infected tissue with the administration of more pure silver colloid at a regular interval designed to maintain the required level of tissue density in order to maintain regional antisepsis. For colds and sinus infections, the nasal aspiration should be repeated at least every thirty (30) to sixty (60) minutes in order for the therapy to be effective. For lower respiratory infections the nebulized inhalation should be repeated for at least three (3) to five (5) minutes every few hours.

This is a treatment intended for the lungs and hence there is far less liquid flow. The replenishment here is not required as often and is primarily intended to overcome the loss of pure ionic silver to binding with anions and proteins in the interstitial fluid. The subject usually inhales from the nebulizing device for at least 5 minutes every 3 hours. The dose tends to be on the order of a couple of milliliters for each 5 minute treatment.

Thus, the droppletized application of the twenty (20) to sixty (60) ppm concentration at the correct replenishment interval provides for a highly effective means of terminating a viral or bacterial infection of tissues in the respiratory tract by maintaining tissue density concentrations of 10 micrograms/ml or greater of pure (uncompound) silver directly at the site. This has demonstrated far greater effectiveness than any current therapy for colds, sinus infections and lower respiratory infections.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. A device for internally treating an illness or infection of tissue of a the upper and lower respiratory tract, the device comprising:

a container holding a predetermined concentration of pure uncompounded aqueous silver colloid substance; and means for delivering appropriately-sized mist droplets of the colloid substance directly to the tissue to maintain a predetermined antimicrobial tissue density concentration of the colloid substance for a predetermined time period.

2. The device of claim 1 wherein the droplets of the colloid substance are sized to negotiate the bend of the esophagus and reach the lower respiratory tract and lungs.

3. The device of claim 1 wherein the droplets of the colloid substance are sized to coat the nasal passageways.

4. A method of infusing an uncompounded silver colloid suspended antimicrobial substance into tissue within the body's respiratory tract, the method comprising:

providing a misting device;

providing the uncompounded silver colloid suspended antimicrobial substance within the misting device;

delivering the colloidal silver suspension in a mist of small droplets directly to the tissue to be treated within the body to obtain a predetermined antimicrobial tissue density concentration; and further redelivering the colloidal silver suspension at predetermined time intervals so as to maintain the antimicrobial tissue density concentration for a predetermined time period.

5. The method of claim 4 and further comprising using a nebulizer to achieve the small droplets necessary to reach the lower respiratory tract.

6. The method of claim 4 and further comprising a nasal spray bottle to achieve the larger droplets necessary to coat the nasal passage ways.

7. The method of claim 4 wherein the predetermined tissue concentration is greater than or equal to ten ($\geqq 10$) micrograms/ml.

* * * * *